(12) United States Patent
Rousseau

(10) Patent No.: US 7,199,246 B2
(45) Date of Patent: Apr. 3, 2007

(54) PROCESS FOR THE PREPARATION OF PESTICIDAL COMPOUNDS

(75) Inventor: Jean-François Rousseau, Saint-Drezery (FR)

(73) Assignee: Merial Limited, Duluth, GA (US)

( * ) Notice: Subject to any disclaimer, the term of this patent is extended or adjusted under 35 U.S.C. 154(b) by 591 days.

(21) Appl. No.: 10/297,676

(22) PCT Filed: Jun. 7, 2001

(86) PCT No.: PCT/EP01/07398

§ 371 (c)(1), (2), (4) Date: Jul. 30, 2003

(87) PCT Pub. No.: WO01/94315

PCT Pub. Date: Dec. 13, 2001

(65) Prior Publication Data

US 2004/0058819 A1    Mar. 25, 2004

Related U.S. Application Data

(60) Provisional application No. 60/210,803, filed on Jun. 9, 2000.

(51) Int. Cl.
  *C07D 231/44*   (2006.01)
  *C07D 41/04*   (2006.01)
(52) U.S. Cl. ............... 546/276.1; 546/366.7; 548/367.4
(58) Field of Classification Search ............ 546/276.1, 546/366.7; 504/253; 548/367.4
See application file for complete search history.

(56) References Cited

U.S. PATENT DOCUMENTS

| | | |
|---|---|---|
| 2,422,400 A | 6/1947 | Farlow |
| 5,232,940 A | 8/1993 | Hatton et al. |
| 5,306,694 A | 4/1994 | Phillips et al. |
| 5,556,873 A | 9/1996 | Huang et al. |
| 6,160,002 A | 12/2000 | Huber et al. |

FOREIGN PATENT DOCUMENTS

| EP | 0215964 | 4/1987 |
|---|---|---|
| EP | 0295117 | 12/1988 |
| EP | 0500209 | 8/1992 |
| WO | 00/35884 | 6/2000 |

OTHER PUBLICATIONS

Kawasaki et al., "Asymmetric Reduction of Prochiral Cyclic Ketones With Lithium Aluminum Hydride Partially Decomposed By (1R,2S)-(-)-N-Methylephedrine And 2-Alkylaminopyridine", *Chemistry Letters*, pp. 239-242 (1984), published by The Chemical Society of Japan, Tokyo, Japan, XP000578114.

*Primary Examiner*—Kamal A. Saeed
(74) *Attorney, Agent, or Firm*—Frommer Lawrence & Haug LLP; Thomas J. Kowalski; Judy Jarecki-Black

(57) ABSTRACT

A process for the preparation of a compound of general formula (I), wherein $R^1$ is CN or $CSNH_2$; $R^2$ is hydrogen or chloride; and $R^3$ is halogen or haloalkyl or haloalkoxy or $SF_5$ which process comprises reacting a compound of formula (II), where $R^1$, $R^2$ and $R^3$ are as defined above; with a proton source.

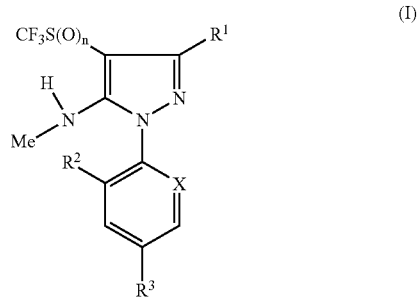

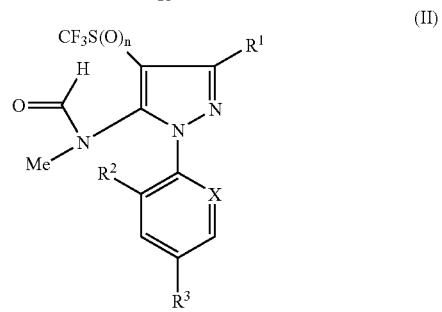

33 Claims, No Drawings

PROCESS FOR THE PREPARATION OF PESTICIDAL COMPOUNDS

This application claims the benefit of U.S. Provisional Patent Application No. 60/210,803, filed Jun. 9, 2000.

The present invention relates to a process for the preparation of substituted pyrazole compounds.

Pyrazoles such as 5-Amino-1-aryl-3-cyanopyrazole compounds and derivatives thereof, for example Fipronil, form an important class of insecticides. Certain substituted 5-N-alkyl-N-alkoxyacetylamino-1-aryl-3-cyanopyrazole compounds have valuable pesticidal properties as disclosed in WO 00/35884 and U.S. Pat. No. 5,556,873.

We have developed a new synthesis route for the production of intermediate compounds useful in the preparation of substituted pyrazole pesticide compounds.

Accordingly, the present invention provides a process for the preparation of a compound of general formula (I)

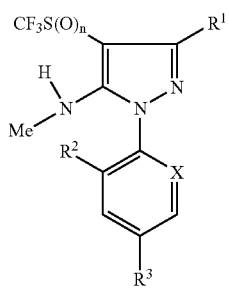

(I)

wherein
R$^1$ is CN or CSNH$_2$;
R$^2$ is hydrogen or chloride; and
R$^3$ is halogen or haloalkyl or haloalkoxy or SP$_5$ which process comprises reacting a compound of formula (II)

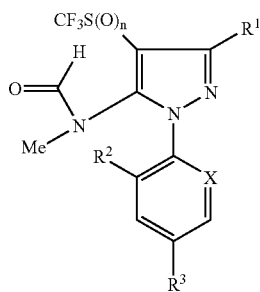

(II)

where R$^1$, R$^2$ and R$^3$ are as defined above; with a proton source.

The proton source used in the process of the present invention is preferably an aqueous acidic solution for example aqueous hydrogen chloride.

The reaction is suitably carried out in a suitable solvent or in a solvent which may or may not be partially miscible with water. Suitable solvents include hydrocarbon solvents such as toluene or xylene.

The amount of proton source used in the reaction is suitably from 0.1 to 2 equivalents, preferably from 0.5 to 1.0 equivalents.

The reaction may suitable be carried out at a temperature of from minus 50 to 200° C., preferably from 50 to 100° C.

With regard to R$^1$, R$^2$ and R$^3$, R$^1$ is preferably CN, R$^2$ is preferably chloride and R$^3$ is preferably a haloalkyl, especially trifluoromethyl.

Compound (II) may be prepared by a novel synthesis route and according to another aspect of the present invention there is provided a process for the preparation of compound (II) as defined above which process comprises reacting a compound of general formula (III).

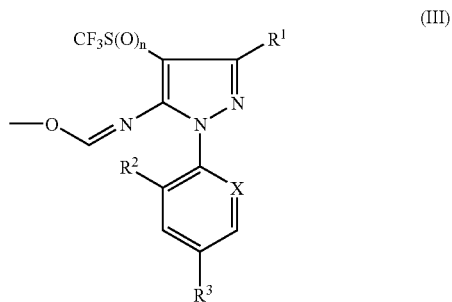

(III)

wherein R1, R2 and R3 are as previously defined; with a quaternary ammonium salt.

The quaternary ammonium salt may be a tetraalkylammonium halide such as the iodide or the bromide, preferably tetraalkylammonium bromide. Suitable tetraalkylammonium bromide include tetrabutylammonium Bromide. The amount of the halide salt used in the reaction is suitably from 0.01 to 2 equivalents, preferably from 0.1 to 0.5 equivalents.

The reaction may be carried out in the presence of an organic solvent which may or may not be partially miscible with water. Suitable solvents include hydrocarbon solvents such as toluene or xylene. The reaction is suitably carried out at a temperature of from 50 to 100° C.

Compound (III), as defined above, may be prepared by the known synthesis route which comprises reacting a pyrazole compound known as fipronil having the formula (IV)

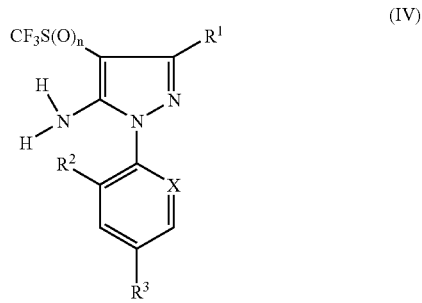

(IV)

with trimethylorthoformate. This reaction may be carried out the presence of an acidic catalyst. Suitable catalyst include para-toluene sulphonic acid.

Compound (III) may also be treated with the quaternary ammonium salt followed by acidic treatment to produce directly compound (I) without isolating compound (II).

Compound (I) may also be prepared by reacting fipronil (compound IV) with formaldehyde or a formaldehyde trimer or the chemical equivalent thereof to produce an intermediate compound (V)

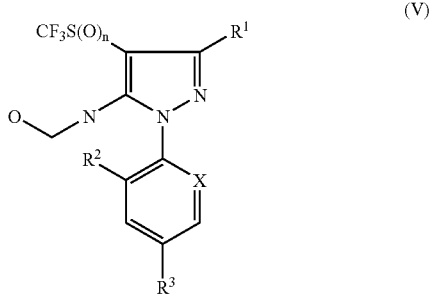

where R1, R2, R3 are as defined above.

Intermediate compound (V) may then be reacted with a reducing agent to provide compound (I). A suitable reducing agent includes sodium borohydride. The reducing agent may be present in an amount of from 1 to 5 equivalents.

Certain compounds according to formulae (II), (III) and (V) are novel compounds and in particular according to another aspect of the present invention there is provided novel compounds:

3-cyano-1-(2,6-dichloro-4-trifluoromethylphenyl)-5-N-formyl-N-methylamino-4-trifluoromethylsulfinylpyrazole (Compound II).

3-cyano-1-(2,6-dichloro-4-trifluoromethylphenyl)-5-methoxymethylideneamino-4-trifluoromethylsulfinylpyrazole (Compound III)

3-cyano-1,(2,6-dichloro-4-trifluoromethylphenyl)-5-hydroxymethylamino-4-trifluoromethylsulfinylpyrazole (Compound V).

Compound (I) prepared according to the process of the present invention may be used as the starting material for a further important pyrazole which is known to have pesticidal properties and which is defined according to general formula (VI).

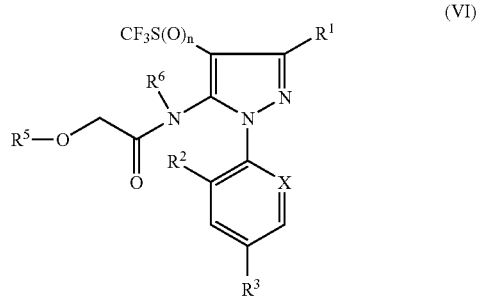

wherein
$R^1$ is CN or $CSNH_2$;
X is N or $CR^4$;
$R^2$ and $R^4$ are, each, independently hydrogen or chlorine;
$R^3$ is halogen, haloalkyl, haloalkoxy or —$SF_5$;
$R^5$ and $R^6$ are each independently an alkyl group; and
n is 0, 1 or 2;

The preparation of this compound from compound (I) is known from International Patent Application Number WO 00/35884 which is herein incorporated by reference. In particular compound (I) is reacted with ethoxy acetyl chloride in the presence of triethylamine to produce compound (VI).

The present invention will now be illustrated by reference to the following non limiting examples:

EXAMPLE 1

A substantial molar excess of trimethylorthoformat is reacted with fipronil (Compound IV) at reflux with 0.5 equivalents of paratoluensulfonic acid to provide 3-Cyano-1-(2,6-dichloro-4-trifluoromethylphenyl)-5-methoxymethylideneamino-4-trifluoromethylsulfinylpyrazole (Compound III).

This product is immediately treadted with 0.1 equivalents of tetrabutylammonium iodide in xylenes at 100 degrees centigrade for 5 hours to provide 3-Cyano-1-(2,6-dichloro-4-trifluoromethylphenyl)-5-(N-formyl-N-methylamino)-4-trifluoromethylsulfinylpyrazole (Compound II). The medium is immediately reacted with aqueous hydrogen chloride and to provide 3-Cyano-1-(2,6-dichloro-4-trifluoromethylphenyl)-5-methylamino-4-trifluoromethylsulfinylpyrazole as final product (Compound I).

EXAMPLE 2

5 equivalent of a sodium methylate (30% solution in methanol) was rapidly added to a suspension of 0.437 g of Fipronil and 1.4 equivalent of paraformaldehyde in 3 mL of methanol to provide the 3-Cyano-1-(2,6-dichloro-4-trifluoromethylphenyl)-5-hydroxymethylamino-4-trifluoromethylsulfinylpyrazole (Compound V) after 3 hour at 20° C. and 1 hour at 60° C. Then 1 equivalent of sodium borohydride was added to the medium which provide after classical extraction and chromatography separation the 3-Cyano-1-(2,6-dichloro-4-trifluoromethylphenyl)-5-methylamino-4-trifluoromethylsulfinylpyrazole (Compound I).

What is claimed is:

1. A process for the preparation of a compound of general formula (I)

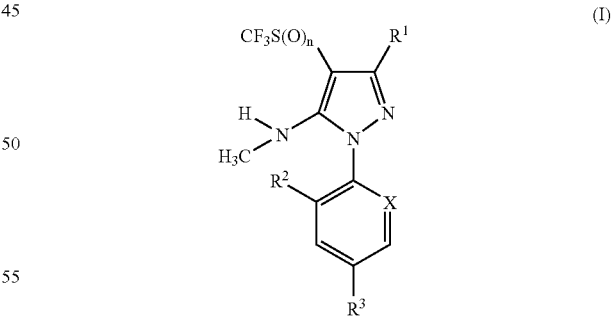

wherein $R^1$ is CN or $CSNH_2$; $R^2$ is hydrogen or chloro; X is N or $CR^4$; $R^4$ is hydrogen or chloro; n is 0, 1 or 2; and $R^3$ is halo, haloalkyl, haloalkoxy or $SF_5$; which process comprises:

(i) reacting a compound of the formula (III)

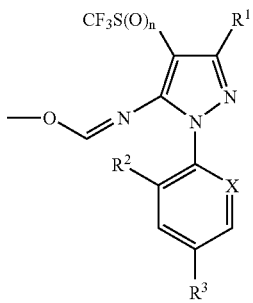

wherein $R^1$ is CN or $CSNH_2$; $R^2$ is hydrogen or chloro; X is N or $CR^4$; $R^4$ is hydrogen or chloro; n is 0, 1 or 2; and $R^3$ is halo, haloalkyl, haloalkoxy or $SF_5$;

with a quaternary ammonium salt to form a compound of the formula (II):

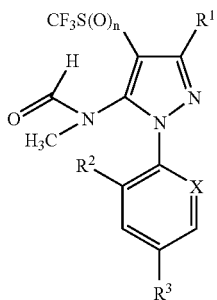

wherein $R^1$, $R^2$, X, n and $R^3$ are as defined above; and (ii) reacting a compound of the formula (II) with a proton source.

2. A process as claimed in claim 1 in which $R^1$ is CN, $R^2$ is chloro, $R^4$ is chloro, X is CCl, n is 1 and $R^3$ is trifluoromethyl.

3. A process as claimed in claim 1 in which the proton source is an aqueous acidic solution.

4. A process as claimed in claim 3 in which the aqueous acidic solution is aqueous hydrogen chloride.

5. A process as claimed in claim 1 in which the reaction is carried out in the presence of a solvent.

6. A process as claimed in claim 5 in which the solvent is toluene or xylene.

7. A process for the preparation of a compound of the formula (II)

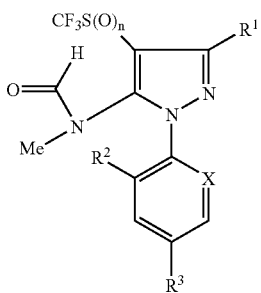

which process comprises reacting a compound of the formula (III)

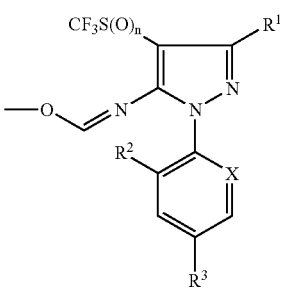

wherein $R^1$ is CN or $CSNH_2$; $R^2$ is hydrogen or chloro; X is N or $CR^4$; $R^4$ is hydrogen or chloro; n is 0, 1 or 2; and $R^3$ is halo, haloalkyl, haloalkoxy or $SF_5$; with a quaternary ammonium salt.

8. A process as claimed in claim 7 in which the quaternary ammonium salt is a tetraalkylammonium halide.

9. A process as claimed in claim 7 in which the tetraalkylammonium halide is tetraalkylammonium bromide.

10. A process as claimed in claim 7 in which the reaction is carried out in the presence of an organic solvent.

11. A process as claimed in claim 10 in which the solvent is toluene or xylene.

12. A process as claimed in claim 1 in which the quaternary ammonium salt is a tetraalkylammonium halide.

13. The compound 3-cyano-1-(2,6-dichloro-4-trifluoromethylphenyl)-5-N-formyl-N-methylamino-4-trifluoromethylsulfinylpyrazole.

14. The compound 3-cyano-1-(2,6-dichloro-4-trifluoromethylphenyl)-5-methoxy methylideneamino-4-trifluoromethylsulfinylpyrazole.

15. A process as claimed in claim 2 in which the proton source is an aqueous acidic solution.

16. A process as claimed in claim 15 in which the aqueous acidic solution is aqueous hydrogen chloride.

17. A process as claimed in claim 2 in which the reaction is carried our in the presence of a solvent.

18. A process as claimed in claim 17 in which the solvent is toluene or xylene.

19. A process as claimed in claim 3 in which the reaction is carried out in the presence of a solvent.

20. A process as claimed in claim 19 in which the solvent is toluene or xylene.

21. A process as claimed in claim 4 in which the reaction is carried out in the presence of a solvent.

22. A process as claimed in claim 21 in which the solvent is toluene or xylene.

23. A process as claimed in claim 15 in which the reaction is carried out in the presence of a solvent.

24. A process as claimed in claim 23 in which the solvent is toluene or xylene.

25. A process as claimed in claim 16 in which the reaction is carried out in the presence of a solvent.

26. A process as claimed in claim 25 in which the solvent is toluene or xylene.

27. A process as claimed in claim 12 in which the tetraalkylammonium halide is tetraalkylammonium bromide.

28. A process as claimed in claim 8 in which the reaction is carried out in the presence of an organic solvent.

29. A process as claimed in claim 28 in which the solvent is toluene or xylene.

30. A process as claimed in claim 9 in which the reaction is carried out in the presence of an organic solvent.

31. A process as claimed in claim 29 in which the solvent is toluene or xylene.

32. A process as claimed in claim 27 in which the reaction is carried out in the presence of an organic solvent.

33. A process as claimed in claim 32 in which the solvent is toluene or xylene.

* * * * *